United States Patent [19]

Johnston et al.

[11] Patent Number: 4,476,064
[45] Date of Patent: Oct. 9, 1984

[54] PHOSPHORUS ACID CATALYST FOR PREPARATION OF 3,9-DICHLORO-2,4,8,10-TETRAOXA-3,9-DIPHOSPHA SPIRO (5,5) UNDECANE

[75] Inventors: Byron E. Johnston, Skillman; Roger P. Napier, Califon, both of N.J.

[73] Assignee: Mobil Oil Corporation, New York, N.Y.

[21] Appl. No.: 453,971

[22] Filed: Dec. 28, 1982

[51] Int. Cl.$^3$ .......................... C07F 9/146; C07F 9/15
[52] U.S. Cl. .................................................. 260/976
[58] Field of Search ........................................ 260/976

[56] References Cited

U.S. PATENT DOCUMENTS 3,192,242 6/1965 Birum .................................. 260/976
3,968,188 7/1976 Birum et al. ........................ 260/976

Primary Examiner—Anton H. Sutto
Attorney, Agent, or Firm—Alexander J. McKillop; Michael G. Gilman; Charles J. Speciale

[57] ABSTRACT

There is provided a process for reacting pentaerythritol with a trivalent phosphorus trihalide conducted in the presence of a phosphorus acid catalyst such as methyl acid phosphate. The reaction product is a useful intermediate for the preparation of flame retardants.

20 Claims, No Drawings

PHOSPHORUS ACID CATALYST FOR PREPARATION OF 3,9-DICHLORO-2,4,8,10-TETRAOXA-3,9-DIPHOSPHA SPIRO (5,5) UNDECANE

BACKGROUND OF THE INVENTION

This application is related to a phosphorus acid catalyst for the preparation of 3,9-dichloro-2,4,8,10-tetraoxa-3,9-diphospha spiro [5,5] undecane.

As shown in U.S. Pat. No. 3,192,242, 3,9-dichloro-2,4,8,10-tetraoxa-3,9-diphospha spiro [5,5] undecane (SPDC) is a useful intermediate for the preparation of effective flame retardants, especially 2,2-bis(-chloromethyl) 1,3-propylene bis[bis(2-chloroethyl) phosphate]. Later, U.S. Pat. No. 3,968,188 claims that certain catalysts effectively convert mixtures of pentaerythritol and phosphorus trichloride to SPDC.

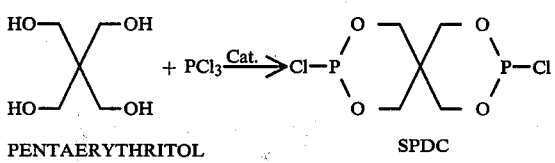

PENTAERYTHRITOL        SPDC

More particularly, U.S. Pat. No. 3,968,188 suggests that SPDC can be obtained by reacting pentaerythritol with a trivalent phosphorus trihalide in the presence of halides of metals of Groups I and II of the Periodic Table, tertiary amines and heterocyclic nitrogen-containing compounds.

The entire disclosures of the above-mentioned U.S. Pat. Nos. 3,192,242 and 3,968,188 are expressly incorporated herein by reference.

SUMMARY OF THE INVENTION

According to one aspect of the invention, there is provided a process for reacting pentaerythritol with a trivalent phosphorus trihalide conducted in the presence of an effective catalytic amount of phosphorus acid catalyst which is at least one compound of the formula

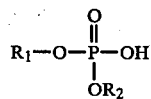

where $R_1$ is a $C_1$–$C_{20}$ hydrocarbyl group and $R_2$ is hydrogen or a $C_1$–$C_{20}$ hydrocarbyl group.

According to another aspect of the invention, there is provided an improved process for the preparation of the pentaerythritol ester of phosphorohalidous acid by the reaction of pentaerythritol and phosphorus trichloride, the improvement comprising conducting the reaction at a pentaerythritol:phosphorus trichloride molar ratio of 1:2 in the presence of a catalytically effective amount of phosphorus acid catalyst which is at least one compound of the formula

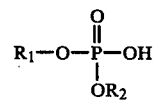

where $R_1$ is a $C_1$–$C_{20}$ hydrocarbyl group and $R_2$ is hydrogen or a $C_1$–$C_{20}$ hydrocarbyl group.

DETAILED DESCRIPTION

The phosphorus acid catalyst compounds of the present invention may be of the formula

where $R_1$ is a $C_1$–$C_{20}$ hydrocarbyl group and $R_2$ is hydrogen or a $C_1$–$C_{20}$ hydrocarbyl group. The $R_1$ and $R_2$ hydrocarbyl groups may be substituted or unsubstituted. Examples of $R_1$ and $R_2$ hydrocarbyl groups include alkyl groups and aryl groups such as phenyl and $C_1$–$C_4$ alkyl substituted phenyl. Preferably, such $R_1$ and $R_2$ alkyl groups are $C_1$–$C_6$ alkyl such as butyl, propyl, ethyl and, especially, methyl. These catalysts may be easily prepared.

A preferred example of a phosphorus acid catalyst is commercially available methyl acid phosphate which is primarily a mixture of mono and di methyl esters of phosphoric acid along with a small amount of phosphoric acid.

The catalyst is used in effective catalytic amounts, e.g., in a concentration of from about 0.005 percent to about 12 percent (based on pentaerythritol), preferably from about 0.05 to about 2 percent by weight.

The preferred mole ratio of the phosphorus trichloride to pentaerythritol required to produce SPDC is 2:1. As a practical matter, slight variations from that ratio are acceptable.

An excess of phosphorus trichloride may be charged initially to make up for losses caused by entrainment with hydrogen chloride during the reaction. Less than the needed amount of phosphorus trichloride, however, may be charged and after elimination of hydrogen chloride is essentially complete, the additional amount of phosphorus trichloride needed to provide the 2:1 molar ratio may be added. The mixture is then warmed until the rearrangement of undesired structures to SPDC is essentially complete. Additional pentaerythritol may, similarly, be added toward the end of the reaction when needed to compensate for initial deficiencies of this reactant. Thus, undesired phosphorus-containing structures that result from a deficiency of either reactant can be readily converted to the desired SPDC structure by adding enough of the deficient reactant to bring the molar ratio of reactants consumed to 2:1 and then warming in the presence of a catalyst described above.

The reactants may be mixed at a temperature of from about 20° C. to about 70° C. and then gradually warmed. A temperature of from about 80° C. to about 125° C. for from about ½ to 2 hours in the presence of an aforedescribed catalyst is generally required to complete the reaction. Preferably, the reaction is heated to a temperatue of from about 90° to about 115° C. and held for ½ to about 2 hours.

The catalyst may be added when the reactants are initially mixed or may be added after the temperature of the reaction mixture has reached about 80° C. or above to promote rearrangement of undesired structures to SPDC. It is preferred to add a small portion of the catalyst when the reactants are initially mixed and then to add the remaining larger portion after the temperature of the reaction has reached about 80° C. or above. The SPDC formed according to the present invention, can be then converted to a desired flame retardant. The catalyst of the present invention is easily prepared, soluble and effective and poses no downstream removal or processing problems in the preparation of flame retardants.

In the process for reacting pentaerythritol with phosphorus trichloride according to the present invention, the phosphorus trichloride reactant may optionally be replaced by phosphorus tribromide.

The phosphorus acid catalyst when used in accordance with the present invention may be completely soluble in the reaction medium. This catalyst may be a pumpable liquid, non hygroscopic, commercially available and highly effective at low (1–2% based on pentaerythritol) levels.

What is claimed is:

1. A process for reacting pentaerythritol with a trivalent phosphorus trihalide conducted in the presence of an effective catalytic amount of phosphorus acid catalyst which is at least one compound of the formula

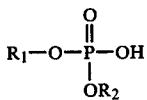  (I)

where $R_1$ is a $C_1$–$C_{20}$ hydrocarbyl group and $R_2$ is hydrogen or a $C_1$–$C_{20}$ hydrocarbyl group.

2. A process according to claim 1, wherein said trivalent phosphorus trihalide is selected from the group consisting of phosphorus trichloride and phosphorus tribromide.

3. A process according to claim 1, wherein the molar ratio of pentaerythritol:phosphorus trihalide is 1:2.

4. A process according to claim 1, wherein $R_1$ is $C_1$–$C_6$ alkyl and $R_2$ is hydrogen or $C_1$–$C_6$ alkyl.

5. A process according to claim 1, wherein said pentaerythritol and phosphorus trihalide are initially combined at a temperature of from about 20° to about 70° C. and then heated to a temperature from about 80° C. to about 125° C.

6. A process according to claim 1, wherein said catalyst is methyl acid phosphate.

7. A process according to claim 3, wherein a molar excess of phosphorus trihalide is initially charged.

8. A process according to claim 1, wherein a molar deficiency of phosphorus trihalide is initially charged.

9. A process according to claim 8, wherein sufficient phosphorus trihalide is subsequently charged to adjust the total molar ratio to about 1:2.

10. A process according to claim 1, wherein a molar deficiency of pentaerythritol is initially charged.

11. A process according to claim 10, wherein sufficient pentaerythritol is subsequently charged to adjust the total molar ratio to about 1:2.

12. In a process for the preparation of the pentaerythritol ester of phosphorohalidous acid by the reaction of pentaerythritol and phosphorus trichloride, the improvement comprising conducting the reaction at a pentaerythritol:phosphorus trichloride molar ratio of 1:2 in the presence of a catalytically effective amount of phosphorus acid catalyst which is at least one compound of the formula

  (I)

where $R_1$ is a $C_1$–$C_{20}$ hydrocarbyl group and $R_2$ is hydrogen or a $C_1$–$C_{20}$ hydrocarbyl group.

13. A process according to claim 12, wherein $R_1$ is $C_1$–$C_6$ alkyl and $R_2$ is hydrogen or $C_1$–$C_6$ alkyl.

14. A process according to claim 12, wherein said pentaerythritol and phosphorus trihalide are initially combined at a temperature of from about 20° to about 70° C. and then heated to a temperature from about 80° C. to about 125° C.

15. A process according to claim 1, wherein said catalyst is methyl acid phosphate.

16. A process according to claim 12, wherein a molar excess of phosphorus trihalide is initially charged.

17. A process according to claim 12, wherein a molar deficiency of phosphorus trihalide is initially charged.

18. A process according to claim 17, wherein sufficient phosphorus trihalide is subsequently charged to adjust the total molar ratio to about 1:2.

19. A process according to claim 12, wherein a molar deficiency of pentaerythritol is initially charged.

20. A process according to claim 19, wherein sufficient pentaerythritol is subsequently charged to adjust the total molar ratio to about 1:2.

* * * * *